United States Patent [19]

Neumaier

[11] 4,224,241
[45] Sep. 23, 1980

[54] PRODUCTION OF HALOGENOMETHYLPHOSPHINIC ACID HALIDES

[75] Inventor: Hubert Neumaier, Hürth, Fed. Rep. of Germany

[73] Assignee: Hoechst Aktiengesellschaft, Fed. Rep. of Germany

[21] Appl. No.: 40,677

[22] Filed: May 21, 1979

[30] Foreign Application Priority Data

May 24, 1978 [DE] Fed. Rep. of Germany ....... 2822655

[51] Int. Cl.² .............................................. C07F 9/34
[52] U.S. Cl. ................................................. 260/543 P
[58] Field of Search ..................................... 260/543 P

[56] References Cited

U.S. PATENT DOCUMENTS 3,360,557  12/1967  Moedritzer ........................ 260/543 P
3,943,170  3/1976   Kleiner ............................. 260/543 P

OTHER PUBLICATIONS

Groenweghe, J.A.C.S., vol. 83, pp. 1811–1813 (1961).
Izvest, Akad. Nauk SSSR, Otdel. Khim. Nauk, 1951, pp. 185–191.
Otdel. Khim. Nauk, 1953, pp. 862–867.

Primary Examiner—Natalie Trousof
Assistant Examiner—James H. Reamer
Attorney, Agent, or Firm—Connolly and Hutz

[57] ABSTRACT

The invention relates to a process for making halogenomethylphosphinic acid halides of the general formula:

$$XCH_2(R)P(O)X$$

in which R stands for an alkyl, halogenoalkyl, aralkyl, halogenoaralkyl, aryl or halogenoaryl group with up to 18 carbon atoms and X stands for a halogen atom. The compounds are made by reacting an organyl-dihalogenophosphane of the general formula:

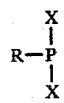

in which R and X have the meanings given above, with trioxane in the presence of a Lewis acid or protonic acid as a catalyst, the reaction being effected at temperatures of 80° to 250° C.

3 Claims, No Drawings

PRODUCTION OF HALOGENOMETHYLPHOSPHINIC ACID HALIDES

The present invention relates to a process for making halogenomethylphosphinic acid halides.

It has already been described that organyldichlorophosphanes can be reacted with formaldehyde to give chloromethylorganylphosphinic acid chlorides in accordance with the folliwing general formula:

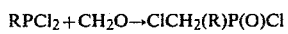

$$RPCl_2 + CH_2O \rightarrow ClCH_2(R)P(O)Cl$$

Thus, for example, by subjecting ethyldichlorophosphane and phenyldichlorophosphane, respectively, to heat treatment with paraformaldehyde in a sealed tube M. I. KABACHNIK and E. S. SHEPELEVA, Otdel. Khim. Nauk 1953, 862-7, were able to obtain the corresponding chloromethylphosphinic acid chlorides in yields of 36 and 47%, respectively. Adverse effects which are typical of this method reside in the fact that the minor quantities of starting material which can be reacted in a sealed tube under pressure need relatively long reaction periods and that the desirable final products are obtained in commercially unattractive yields. A further process has been described by L. D. C. GROENWEGHE and J. H. PAYNE, J.A.C.S. 83, 1811-13 (1961), wherein paraformaldehyde is added in small metered portions to boiling methyldichlorophosphane to give chloromethylmethylphosphinic acid chloride in a 70% yield. This process is also not free from adverse effects. They reside in the formation of considerable quantities of by-products which impair the yield of desirable product and in the fact that commercial operation is rendered difficult inasmuch as the strongly exothermal reaction makes it necessary for the paraformaldehyde to be introduced in small portions into the reaction mixture. This however means long reaction periods.

The present invention now unexpectedly provides a process for making halogenomethylphosphinic acid halides of the general formula:

$$XCH_2(R)P(O)X \quad (I)$$

in which R stands for an alkyl or halogenoalkyl, an aralkyl or halogenoaralkyl, an aryl or halogenoaryl group with up to 18 carbon atoms and X stands for a halogen atom, the chlorides being obtained in very good yields, which comprises: reacting an organyldihalogenophosphane of the general Formula:

$$\begin{array}{c} X \\ | \\ R-P \\ | \\ X \end{array} \quad (II)$$

in which R and X have the meanings given above, with trioxane in the presence of a catalyst consisting of a Lewis acid or a protonic acid, the reaction being effected at temperatures of 80° to 250° C., preferably 110° to 170° C.

In the above formulae, R stands more preferably for an unsubstituted alkyl group or for a group in which one or more hydrogen atoms are replaced by a halogen with 1 to 10, preferably 1 to 4 carbon atoms. The useful substituents comprise more specifically the methyl, ethyl, halogenomethyl and halogenoethyl groups as well as cycloalkyl groups with 5 to 8 carbon atoms, especially the cyclohexyl group which may also contain halogen, and also aryl or aralkyl groups with 6 to 10 carbon atoms, especially the phenyl or phenylalkyl group, in which one or more hydrogen atoms may equally be replaced by halogen.

X which generally stands for halogen, stands more preferably for bromine and especially for chlorine.

The useful Lewis acids comprise, for example, aluminium chloride, tin tetrachloride, borofluoride etherate and the useful protonic acids comprise, for example, phosphoric acid, sulfuric acid, hydrogen bromide or hydrogen chloride. It is particularly advantageous to use gaseous hydrogen bromide and hydrogen chloride as these are compounds which are easy to pass through the reaction mixture and leave no residues during work-up.

The reaction should preferably be carried out without solvent. It is, however, possible for it to be carried out in the presence of a solvent, which should conveniently be employed in all those cases in which use is made of solid organyldichlorophosphane.

The reaction has been found to occur very rapidly in the presence of a catalyst and is terminated within about 0.25 to 3 hours in customary production facilities, depending on their dimensions and the reaction temperature selected. It is particularly advantageous to effect the reaction continuously as the rapid reaction in combination with the high conversion rate enables very high space/time-yields to be obtained, in the absence of solvents.

To carry out the reaction, it is good practice to dissolve trioxane in an organyldihalogenophosphane and to introduce metered portions of the solution at a preselected temperature into a reactor through which hydrogen halide is passed so as to establish a hydrogen halide atmosphere therein. It is also advantageous to feed the reactor with a portion of reaction product from a previous batch, heat the reaction product portion to the reaction temperature selected and admix it with metered portions of the solution which is to undergo reaction. In all those cases in which the reaction is carried out continuously, it is good practice to remove reaction product from the reactor at the same rate as feed solution is admitted thereto.

A further advantageous feature provides for the reactants to be used in stoichiometric proportions, i.e. for 3 mols of organyldihalogenophosphane to be used per mol of trioxane or for 1 mol of organyldihalogenophosphane to be used per mol of a unit of the formula [—CH₂—O—]. It is naturally possible to use an excess of one reactant or other. The use of an excess of trioxane has, however, been found to give rise to the formation of higher boiling by-products which impair the yield, while the use of an excess of organyldihalogenophosphane on the other hand has been found to leave unreacted portions which boil under reflux and reduce the reaction temperature. Needless to say this has adverse effects on the reaction velocity and on the conversion of the dihalogenophosphane of which increasing portions remain unreacted if the reaction temperature is further reduced.

The reaction produces good or very good yields of desirable product. In all those cases in which phosphinic acid halides are used as intermediates only, it is therefore possible to employ the crude product for further reaction and work-up. In all other cases, it is possible to purify the phosphinic acid halides by subjecting them to distillation, for example.

The phosphinic acid halides made by the process of the present invention are intermediates of particular interest in the production of plant protecting agents, flameproofing materials and pharmaceutical preparations.

EXAMPLE 1

Specimens of $CH_3PCl_2$ and trioxane (molar ratio =3:1) admixed with various Lewis acids and protonic acids, respectively, and specimens left free from catalyst, were heated for about 3 hours under reflux. Next, the formation of $ClCH_2(CH_3)P(O)Cl$ was identified by H-NMR-spectroscopy. The boiling point of the mixture which was free from catalyst remained constant (85° C.) and phosphinic chloride could not be found to have been formed. After the addition of the catalyst, the reflux temperature of the various specimens increased and acid chlorides were obtained.

| Catalyst | Temperature increase observed | $ClCH_2(CH_3)P(O)Cl$ identified |
|---|---|---|
| (a) — | — | — |
| (b) $H_2SO_4$ | + | + |
| (c) $AlCl_3$ | + | + |
| (d) $BF_3 \cdot E_2O$ | + | + |
| (e) $SnCl_4$ | + | + |
| (f) HCl | ++ | ++ |

+ +very distinctly observed or identified

EXAMPLE 2

50 g of chloromethyl-methylphosphinic acid chloride was placed in a round flask provided with a reflux condenser, thermometer, dropping funnel and gas inlet, heated to 150° C. therein and hydrogen chloride gas (10 l/h) was passed therethrough. Next, a solution of 450 g (5 mols) of trioxane in 1755 g (14.17 mols) of methyldichlorophosphane of 94.5% strength was added dropwise through the dropping funnel within 215 minutes so that the temperature did not substantially exceed 150° C. Hydrogen chloride gas was passed through the reactants over the entire reaction period. H-NMR-spectroscopy after the reaction showed the formation of chloromethylmethylphosphinic acid chloride which was obtained together with a minor proportion of chloromethyl-methylphosphinic anhydride. Phosgene was then introduced over 2 hours at 150° C. and the anhydride was thereby converted to desirable final product. The reaction product was purified by distillation under vacuum. 23.5 g (0.2 mol) of unreacted methyldichlorophosphane was obtained first and then, at 66° C. under a pressure of 0.5 millibar, 1964 g of pure chloromethyl-methylphosphinic acid chloride. $ClCH_2(CH_3)P(O)Cl$ was obtained in a yield of 93.2% for a 98.6% conversion of $CH_3PCl_2$, the 50 g of feed material being deducted. The product was subjected to H-NMR-spectroscopy but could not be found to contain impurities.

EXAMPLE 3

Example 2 was repeated but the reaction temperature was 130° C. The reaction product was purified by distillation. Altogether 1929 g of chloromethyl-methylphosphinic acid chloride was obtained together with 107.5 g (0.93 mol) of unreacted $CH_3PCl_2$. $ClCH_2(CH_3)P(O)Cl$ was obtained in a yield of 96.4% for a 93.5% conversion of $CH_3PCl_2$, the 50 g of feed material being deducted.

The product was subjected to H-NMR-spectroscopy but could not be found to contain impurities.

EXAMPLE 4

A circulation reactor comprised of two jacketed tubular structures in upright position, which were connected together at their lower and upper ends, was filled with chloromethyl-methylphosphinic acid chloride and heated to 150° C. 10 l/h of hydrogen chloride gas was introduced into the bottom portion of one of the said two tubular structures so that the material therein was forced to circulate therethrough. Mounted on the top of the reactor was a reflux condenser for the removal of hydrogen chloride gas.

A solution was prepared from methyldichlorophosphane and trioxane in a ratio by weight of 3.9:1 (molar ratio =3:1). 1.7 kg/h of said solution (this corresponded to 1353 g or 11.56 mols of $CH_3PCl_2$ and 347 g or 3.85 mols of trioxane per hour) was continuously metered into the reactor which was maintained at a constant temperature of 150° C. At the same time, 1.7 kg/h of reaction product was taken from the reactor via an overflow and delivered to a continuously operated vacuum distilling column (18.5 millibars). 1.54 kg or 10.47 mols of chloromethyl-methylphosphinic acid chloride was obtained per hour near the column head. Placed upstream of the vacuum pump was a cooling trap ($-78°$ C.) in which 64.3 g or 0.55 mol of unreacted $CH_3PCl_2$ was condensed per hour.

95.25% of the $CH_3PCl_2$ accordingly underwent conversion and chloromethyl-methylphosphinic acid chloride was obtained in a yield of 95.1%.

EXAMPLE 5

30 g (0.33 mol) of trioxane was dissolved in 131 g (1 mol) of ethyldichlorophosphane $C_2H_5PCl_2$ (briefly termed EDP hereinafter). An about 30 cm³ portion of the solution was placed in a glass flask, which was provided with a reflux condenser, dropping funnel and tubular gas inlet, heated to 110° C. therein while 5 l/h of HCl gas was passed through. The temperature increased to 143° C. The flow of HCl through the solution was maintained and the balance portion of the solution was added dropwise within 90 minutes while the temperature was maintained. After a post-reaction period of 30 minutes, the reaction mixture was distilled unter vacuum. The first runnings consisted substantially or unreacted EDP and chloromethyl-ethylphosphinic acid chloride was obtained in a yield of 94.7 g corresponding to 77.8%, based on a 75.6% conversion of EDP.

EXAMPLE 6

15 g (0.17 mol) of trioxane was dissolved in 89.5 g (0.5 mol) of phenyldichlorophosphane ($C_6H_5PCl_2$) and the solution was introduced dropwise within 2.5 hours into a flask heated to 150° C. At the same time, 5 l/h of hydrogen chloride was passed through the solution. After termination of the reaction, the reaction product was distilled under vacuum. 16 g of $C_6H_5PCl_2$ was obtained as the first runnings. 65 g of $C_6H_5(ClCH_2)P(O)Cl$ was obtained at 136° C. under a pressure of 0.9 millibar. This corresponded to a yield of 75.8%, based on the $C_6H_5PCl_2$ which underwent conversion.

We claim:

1. A process for making halogenomethylphosphinic acid halides of the general formula:

XCH$_2$(R)P(O)X in which R stands for a methyl, ethyl, phenyl, halogenomethyl, halogenoethyl or halogenophenyl group and X stands for a halogen atom, which comprises: reacting an organyldihalogenophosphane of the general formula:

in which R and X have the meanings given above, with trioxane in the presence of aluminum-III-chloride, tin-IV-chloride, borofluoride etherate, phosphoric acid, sulfuric acid, hydrogen bromide or hydrogen chloride as a catalyst, the reaction being effected at temperatures of 80° to 250° C.

2. A process as claimed in claim 1, wherein the organyldihalogenophosphane is selected from the corresponding chloro- or bromophosphanes.

3. A process as claimed in claim 1, wherein the reaction is effected at temperatures of 110° to 170° C.